United States Patent [19]

Wagner

[11] 4,401,616
[45] Aug. 30, 1983

[54] METHOD FOR MAKING CUSTOM DENTAL IMPRESSION TRAYS

[76] Inventor: John W. Wagner, 8001 Lakemont Dr. NE., Seattle, Wash. 98115

[21] Appl. No.: 294,084

[22] Filed: Aug. 19, 1981

[51] Int. Cl.³ .................. B29C 17/02; B29C 17/10
[52] U.S. Cl. .................................... 264/138; 264/16; 264/219; 264/322; 264/339
[58] Field of Search ............... 264/16, 320, 322, 292, 264/339, 219, 222, 227; 264/138, 157, 160

[56] References Cited

U.S. PATENT DOCUMENTS

| | | | |
|---|---|---|---|
| 2,218,710 | 10/1940 | Hermann et al. | 128/90 |
| 2,948,634 | 8/1960 | Furendal et al. | 128/90 |
| 3,302,642 | 2/1967 | Allen | 128/90 |
| 3,303,844 | 2/1967 | Johnson et al. | 264/16 |
| 3,360,800 | 1/1968 | Roland | 264/16 |
| 3,692,023 | 9/1972 | Phillips et al. | 128/90 |
| 3,739,052 | 6/1973 | Ayres et al. | 264/322 |
| 4,044,762 | 8/1977 | Jacobs | 264/16 |
| 4,227,877 | 10/1980 | Tureaud et al. | 433/37 |
| 4,235,594 | 11/1980 | Schwartz | 433/68 |
| 4,240,415 | 12/1980 | Wartman | 128/90 |

Primary Examiner—Willard E. Hoag
Attorney, Agent, or Firm—Robert W. Beach; Ward Brown

[57] ABSTRACT

A flat uniform thickness or flat sheet of thermoplastic material is heated to deformable, nonresilient, nonliquid condition, shaped over a built-up study model of the jaw ridge of a patient requiring a dental prosthesis and cooled to substantially rigid condition to form a custom dental impression tray.

1 Claim, 7 Drawing Figures

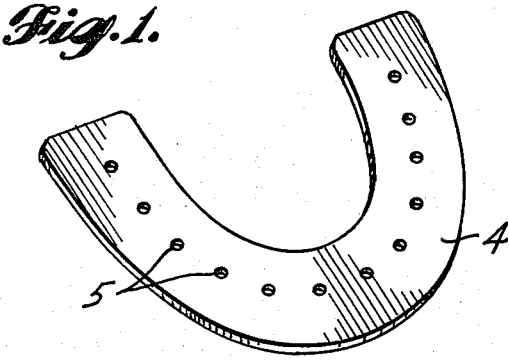
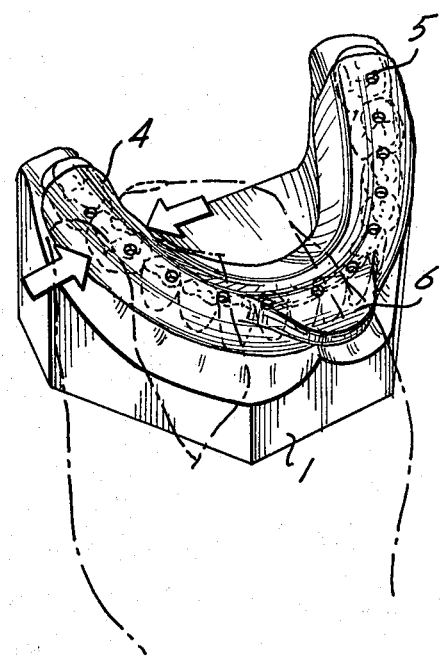
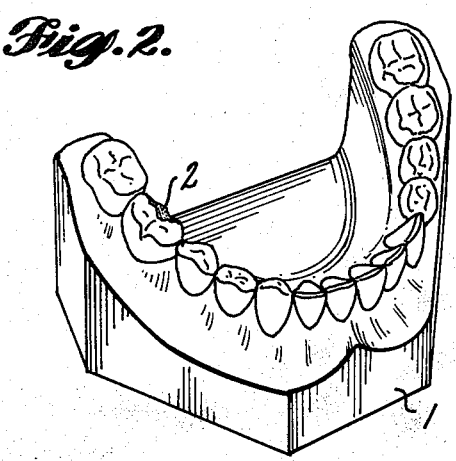
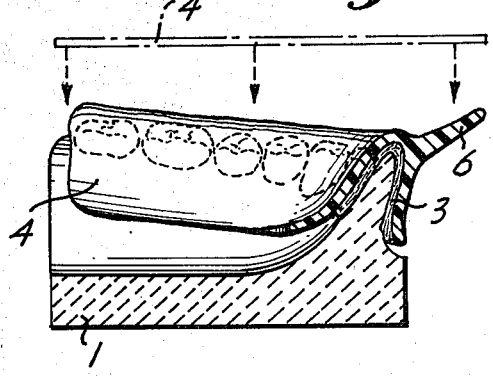
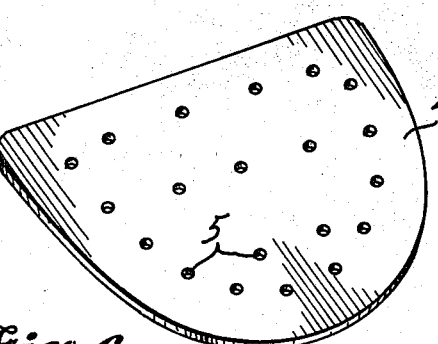
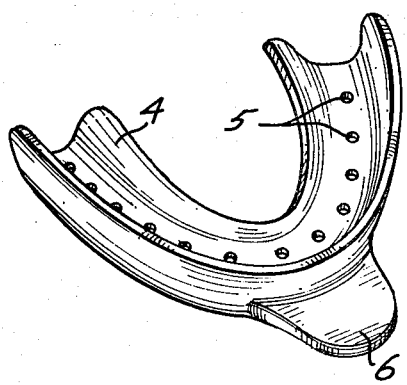
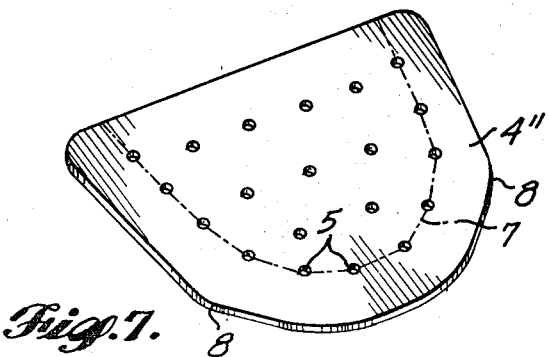

4,401,616

METHOD FOR MAKING CUSTOM DENTAL IMPRESSION TRAYS

BACKGROUND OF THE INVENTION

1. Field of the Invention

The present invention relates to a method of making custom dental impression trays.

2. Prior Art

A denture, bridge, or cap or crown—or an accurate wax replica of such a dental prosthesis used in the manufacture of the finished prosthesis—usually is formed on a full size model of a patient's jaw ridge, that is, the ridge-formed parts of the gums, the adjacent teeth, if any, and the alveolar portions of the jaws, in the area to receive the prosthesis. A mold for the initially plastic material which hardens into such a model is obtained by taking an impression of the appropriate area of the patient's jaw ridge.

The appearance and, particularly, the fit of the finished prosthesis depends to a large degree on the preciseness of the model on which it was formed which, in turn, depends on the preciseness of the impression taken of the patient's jaw ridge in forming the mold for the model. Even a small error in the impression can ultimately result in an unstable or gum-irritating denture or a bridge or crown which causes adjacent tissue to be irritated or to recede.

Typically the deformable impression material is held in a tray having an arcuate channel or depression of a width slightly or substantially greater than the width of the jaw ridge in the area to receive the prosthesis. The tray containing the deformable impression material is placed in the patient's mouth, then is pressed firmly so that it surrounds the jaw ridge, causing the impression material to conform to the shape of the gums and teeth, and, after the impression material has hardened in contact with the gums and teeth, is removed from the patient's mouth so that the hardened impression material can be used as the mold for the model.

Since some of the tissues of which an impression is required are quite soft, the impression material used must be even softer to prevent distortion of the tissues as the impression material is pressed into contact with such tissues. The softness of the tissues also makes it extremely important that the impression tray correspond closely to the size and shape of the area to receive the prosethesis. As noted by C. W. Ellinger et al. at page 110 of their book *Synopsis of Complete Dentures* (Lea & Febiger, 1975), "An impression tray is the most important part of an impression, regardless of technique." If at any location the overall width of the tray is too great, or the width of the tray channel is too narrow, the gum tissues are stretched or compressed by the tray leading to an inaccurate impression. As stated at page 111 of *Synopsis of Complete Dentures*, Since all edentulous ridges vary, it would seem that the ideal tray is one that is specifically made for the patient. The borders of this tray can be adjusted so that they control the movable soft tissues around the impression with little distortion to these tissues. At the same time, space may be provided inside the tray consistent with the characteristics of the impression material being utilized.

The word "custom" is used herein to describe such an impression tray made specifically for an individual patient.

*Synopsis of Complete Dentures*, particularly in Chapter 10, also discusses several alternative methods for forming a custom dental impression tray. In each instance a preliminary impression is taken by use of a "stock" tray which may be available in three or four standard sizes. If plastic modeling compound is used as the preliminary impression material, the hardened compound can be removed from the tray, trimmed to the desired thickness and height, and the concave impression "relieved" by scraping or cutting away the hardened compound at desired locations leaving room for the final impression material. In this method the preliminary impression itself is used as the custom tray, and the custom tray is used to obtain a final impression which serves as the mold for the "master" model on which the dental prosthesis is formed.

A problem with this method is that the trimmed, hardened modeling compound is somewhat brittle. It is difficult to apply the localized pressure required to obtain a good final impression without breaking the trimmed hardened tray. As a result, a more popular method for making a custom impression tray is to use the initial impression as a mold for a "study" model on which a custom tray of acrylic resin can be formed.

Unfortunately formation of the acrylic resin custom tray is cumbersome and time consuming. The method recommended in *Synopsis of Complete Dentures* at pages 130 to 131 includes:

taking a preliminary impression as discussed above;

casting the study model using the preliminary impression as the mold;

using the study model to form a "record base" or "baseplate" of shellac of a desired thickness which, in effect, duplicates the prelimary impression in a harder, thinner material, and removing the baseplate from the study model;

building up desired locations of the study model by use of wax;

inverting the baseplate into a soft patty of dental stone and, after the dental stone has hardened, removing the baseplate from the hardened stone, thereby forming an approximate mold or "former" for the custom impression tray;

coating the dental stone tray mold with a separating agent, such as petroleum jelly;

mixing acrylic resin according to the manufacturer's instructions, allowing the initially substantially liquid resin to set to the "doughy" stage and distributing the doughy acrylic resin evenly in the mold; and removing the acrylic resin from the mold while it is still pliable, placing it over the built-up study model, manually adapting it to the study model and allowing the acrylic resin to harden to form the custom tray.

By building up the study model, the resulting custom dental impression tray has room for the final impression material.

Regardless of the method used for manufacturing the custom dental impression tray, such tray is used to obtain a final impression which serves as the mold for making the highly accurate master model on which the dental prosthesis is formed.

SUMMARY OF THE INVENTION

The principal object of the present invention is to provide a simple, quick, inexpensive method of making a dental impression tray closely appoximating the shape and size of a specific patient's jaw ridge and usable to obtain a precise impression of such ridge, including associated soft tissue, for use as a mold in manufacture of an accurate model on which a dental prosthesis can be formed.

In the preferred embodiment of the invention, this object is accomplished by taking a preliminary impression and using it in casting a study model of the jaw ridge, then building up the study model in desired locations, heating a flat uniform thickness sheet blank of thermoplastic material substantially rigid or hard at room temperature but nonresiliently bendable and deformable when heated, manually bending the heated flat sheet blank over the built-up study model and allowing the bent sheet blank to cool to substantially rigid condition.

A definition of "sheet" given in *Webster's Third New International Dictionary Unabridged* that is applicable to the sheet blank of this invention is "5: a broad thinly expanded portion of metal or other substance—b. a portion of metal less than about a quarter or sometimes an eighth of an inch in thickness."

BRIEF DESCRIPTION OF THE DRAWINGS

FIG. 1 is a top perspective of a precut thermoplastic flat sheet blank usable in accordance with the present invention in the manufacture of a custom dental impression tray.

FIG. 2 is a top perspective of a mandibular cast or study model including a chipped first molar.

FIG. 3 is a somewhat diagrammatic top perspective of the thermoplastic flat sheet blank shown in FIG. 1 and the study model shown in FIG. 2 illustrating molding of such flat sheet blank to the study model to form the custom dental impression tray;

FIG. 4 is a somewhat diagrammatic section taken along line 4—4 of FIG. 3; and

FIG. 5 is a top perspective of the resulting custom dental impression tray removed from the study model.

FIGS. 6 and 7 are corresponding top perspectives of alternative precut thermoplastic flat sheet blanks usable in accordance with the present invention in manufacture of a custom dental impression tray.

DETAILED DESCRIPTION

The preliminary steps of manufacturing a custom dental impression tray in accordance with the method of the present invention are conventional, namely: filling a stock dental impression tray, which may be steel, with suitable impression material, such as alginate, and obtaining a preliminary impression of the area of a patient's jaw ridge to receive a dental prosthesis. As also is conventional, the preliminary impression is used as a mold for making a study model of, for example, plaster, which is an approximate replica of the jaw ridge. The study model is used in forming a custom dental impression tray as described below. A highly precise final impression is taken by use of the custom tray using, for example, rubber base as the final impression material, and the final impression is used as a mold for a correspondingly precise master model of, for example, die stone. The dental prosthesis, be it a partial or complete denture, a bridge, or a cap or a crown, or a wax replica of the prosthesis, then can be formed on the master model as is conventional.

The study model 1 of the mandibular ridge of a patient having a chipped first molar 2 requiring a crown is shown in FIG. 2. In accordance with the present invention, the ridge of the study model is padded or built up on both sides with a composite layer 3 of a number of overlying tissue paper sheets of an aggregate thickness of about 1 mm to 3 mm laterally of both sides of the ridge, as best seen in FIG. 4 to allow room for the final impression material in the completed custom tray. A substantially rigid or hard thermoplastic sheet, which may have through perforations 5, is cut to form a flat uniform thickness U-shaped sheet blank, as shown in FIG. 1, with the centerline of the U corresponding approximately to the centerline of the mandibular ridge represented by the study model. The cut flat sheet blank is heated beyond its softening temperature and, as indicated in FIG. 3, is deformed over the built-up study model and manually depressed downward over the study model to a tray form having an arch-shaped concave depression of substantially the same shape but slightly larger than the portion of the study model jaw ridge, as shown in FIG. 4. Preferably a handle 6 is squeezed outward from about the center of the tray shaped blank. Upon cooling, material of the flat sheet blank deformed to tray shape returns to its substantially rigid condition, to retain the tray form shown in FIG. 5.

The resulting substantially rigid or hard custom dental impression tray then is ready for use in obtaining a final impression from the patient. The perforations 5 through the completed custom dental impression tray may be desirable for allowing escape of excess final impression material and for good adhesion of the final impression material to the custom tray. Previously drilling holes through a completed acrylic resin custom tray was required.

The thermoplastic material must be substantially rigid or hard and tough at room or ambient and body temperatures so as to form a sturdy custom dental impression tray of definite shape. The softening temperature should be low enough, however, preferably no greater than about 145° F. (63° C.) to about 160° F. (71° C.), that the flat sheet blank can be handled manually in deformable condition. In heated condition, the blank should be nonresilient and nonliquid so as to maintain its shape as it is deformed around the study model and so as to retain the through perforations; yet when heated it should be sufficiently deformable that the handle 6 can be formed at the front. In addition, the flat sheet blank should be thin enough, its thickness preferably being no greater than about 3/16 inch (4.8 mm), so as to prevent deformation of soft tissue as the final impression is taken, yet thick enough, its thickness preferably being at least about 1/16 inch (1.6 mm), so as to be easily handled and sufficiently strong or tough to withstand the pressure of taking the final impression.

The thermoplastic flat sheet material manufactured by Rolyan Manufacturing Co. Inc. of Menomonee Falls, Wisconsin, under its trademark "Polyform" in a thickness of about ⅛ inch (3.2 mm) meets all of the above requirements and is the preferred material to be used in practice of the present invention. It is substantially rigid or hard and tough at body and ambient temperatures but is deformable, nonresilient and nonliquid when heated to a temperature between about 145° F. (63° C.) and about 160° F. (71° C.). It retains its shape sufficiently when heated that the perforations 5 drilled or punched through it prior to heating are not filled in during deformation of the heated flat sheet blank. The exterior surfaces of the heated blank cool quite rapidly so that it can be handled manually while still deformable.

Additional advantages of the Rolyan Manufacturing Co. Inc. Polyform material are that it is nonbrittle, i.e. tough, both before being heated and after cooling, and it may be cut easily with a sharp knife or scissors for trimming the substantially planar flat sheet blank before it is heated or the resulting custom dental impression tray after it is cooled. The thermoplastic Polyform material also may be reheated repeatedly to soften it and recooled to harden it if, for example, upon examination it is found that the first effort at forming a precise custom dental impression tray with room for the final impression material has failed. The low softening temperature of the preferred material lends it to convenient heating and softening by immersion in hot water. It may be cooled rapidly by dipping it in cold water or by running cold water over it.

Preparation of a patient's tooth or teeth for crowns or bridges, for example, such as by drilling or grinding, can be completed after taking of the initial impression, whereupon the custom tray is used in obtaining a final impression which is used as the mold for the master model on which the prosthesis or a wax replica of the same is formed. Possibly the study model can be made and the custom tray formed while drilling or grinding is carried out, so that only a single sitting is required to obtain both impressions.

Substantially the same procedure is followed in the case of partial or complete mandibular dentures in which the U-shaped thermoplastic flat sheet blank is deformed around the study model of the edentulous mandibular ridge. In the case of maxillary dentures, however, a precise impression of the palate also is required. In that instance, as indicated in FIG. 6, the shape of the precut thermoplastic flat sheet blank 4' will be semielliptical and the blank will be of a width substantially greater than the edentulous maxillary ridge. The study model will include an approximate replica of the palate which also is packed with a thin layer of wax or tissue paper. The thermoplastic flat sheet blank is heated and deformed around the edentulous maxillary ridge with the central portion of the blank being pressed downward in contact with the built-up replica of the palate.

The thermoplastic flat sheet blank 4" shown in FIG. 7 is generally in the shape of a trapezoid rather than being semielliptical. As compared to the tooth arch for which the flat sheet blank 4" was designed, indicated by the broken line 7 in FIG. 7, the periphery of the flat sheet blank approximates the shape of the tooth arch except in the areas of the protuberances 8 at corresponding locations at opposite sides of the sheet blank such that the portion of the flat sheet blank outward of the line 7 is wider in the areas of the protuberances 8 than in other areas. Such protuberances correspond to the locations of the protruding maxillary canines, should the patient still have the same, so that there will be sufficient material to mold over the study model in the areas of the canines.

In other respects the flat sheet blanks of FIGS. 6 and 7 are identical to the flat sheet blank of FIG. 1.

Performed as described above, the method of the present invention is much less time-consuming, expensive and messy than the cumbersome conventional practice of forming an acrylic resin custom dental impression tray, yet results in a hard sturdy or tough, thin tray corresponding closely to the shape and size of a patient's jaw ridge in the area to receive a dental prosthesis.

I claim:

1. The method for making, on a study model of the patient's jaw ridge portion, a custom dental impression tray used for taking a precise final impression of at least that portion of a jaw ridge of a patient to receive a dental prosthesis, which method comprises precutting a flat sheet of thermoplastic material to form a flat sheet blank of a thickness 1/16 inch (1.6 mm) to 3/16 inch (4.8 mm) having a generally arcuate outer periphery and being of a width great enough to overhang the opposite outer lateral margins of the jaw ridge portion of the study model, building up the study model of the jaw ridge portion by packing successive overlying layers of thin tissue paper spacing material onto the model and thereby forming a composite layer having a total thickness of about 1 mm, to 3 mm, approximately equal to the desired thickness of final impression material to be used in the tray in taking the jaw ridge final impression, heating the flat sheet blank of thermoplastic material hard and tough at ambient temperatures until it reaches a deformable, nonresilient, nonliquid condition, manually shaping the heated flat sheet blank into a tray by deforming it onto the built-up study model so as to form a through closely complemental to the shape of at least a portion of the jaw ridge portion of the built-up study model but spaced from the model by the composite packing layer built up on it, and cooling the shaped tray sufficiently that the thermoplastic material returns to its hard and tough condition to preserve its shaped form for use as a custom dental impression tray.

* * * * *

UNITED STATES PATENT AND TRADEMARK OFFICE
CERTIFICATE OF CORRECTION

PATENT NO. : 4,401,616
DATED : August 30, 1983
INVENTOR(S) : John W. Wagner

It is certified that error appears in the above-identified patent and that said Letters Patent are hereby corrected as shown below:

Title page, [56] References Cited, cancel "3,360,800" and insert ---3,360,860---; [57] Abstract, first line, after "sheet" insert ---blank---.

Column 1, line 14, cancel "ridge-formed" and insert ---ridge-forming---.

Column 6, line 43, cancel "through" and insert ---trough---.

Signed and Sealed this

*Eighth* Day of *November 1983*

[SEAL]

*Attest:*

GERALD J. MOSSINGHOFF

*Attesting Officer*     *Commissioner of Patents and Trademarks*